United States Patent

Berenstein et al.

[11] Patent Number: 5,817,057
[45] Date of Patent: Oct. 6, 1998

[54] FLUID PROPULSION STEERABLE CATHETER AND METHOD

[75] Inventors: Alejandro Berenstein, New York, N.Y.; Howard E. Preissman, Los Gatos, Calif.

[73] Assignee: Micro Interventional Systems, Inc., Sunnyvale, Calif.

[21] Appl. No.: 710,133

[22] Filed: Sep. 13, 1996

[51] Int. Cl.⁶ .................................................. A61M 37/00
[52] U.S. Cl. .............................. 604/95; 604/96; 604/102; 606/108
[58] Field of Search ................................ 604/95, 96, 102, 604/156, 264, 280; 128/657; 600/157; 606/108

[56] References Cited

U.S. PATENT DOCUMENTS

| | | |
|---|---|---|
| 3,557,780 | 1/1971 | Sato . |
| 3,995,623 | 12/1976 | Blake et al. . |
| 4,024,873 | 5/1977 | Antoshkiw et al. . |
| 4,403,985 | 9/1983 | Boretos ..................................... 604/95 |
| 4,475,902 | 10/1984 | Schubert ..................................... 604/95 |
| 4,563,181 | 1/1986 | Wijayarathna et al. . |
| 4,696,304 | 9/1987 | Chin . |
| 4,717,381 | 1/1988 | Papantonakos ........................... 604/95 |
| 4,771,777 | 9/1988 | Horzewski et al. . |
| 4,774,366 | 9/1988 | Grakauskas et al. . |
| 4,813,934 | 3/1989 | Engelson et al. . |
| 4,848,344 | 7/1989 | Sos et al. . |
| 4,863,442 | 9/1989 | DeMello et al. . |
| 4,886,506 | 12/1989 | Lovgren et al. . |
| 4,888,364 | 12/1989 | Graiver et al. . |
| 4,943,618 | 7/1990 | Stoy et al. . |
| 5,061,254 | 10/1991 | Karakelle et al. . |
| 5,147,370 | 9/1992 | McNamara et al. . |
| 5,171,221 | 12/1992 | Samson . |
| 5,209,727 | 5/1993 | Radisch, Jr. et al. . |
| 5,225,120 | 7/1993 | Gravier et al. . |
| 5,308,342 | 5/1994 | Sepetka et al. . |
| 5,318,032 | 6/1994 | Lonsbury et al. . |
| 5,336,205 | 8/1994 | Zenzen et al. . |
| 5,337,730 | 8/1994 | Maguire .................................. 600/157 |
| 5,665,063 | 9/1997 | Roth et al. ................................ 604/96 |

*Primary Examiner*—Mark Bockelman
*Assistant Examiner*—Ellen Tao
*Attorney, Agent, or Firm*—Townsend and Townsend and Crew LLP

[57] ABSTRACT

The invention provides flow directed catheters and methods which are useful in introducing various fluids to a target site within a body lumen. In one exemplary embodiment, a flow directed catheter is provided which comprises a catheter body having a proximal end, a distal end and at least one axial lumen. At least one jet is in fluid communication with the axial lumen. The jet is angled toward the proximal end of the catheter body so that a fluid which is flowed through the axial lumen exits the jet to distally propel the catheter body.

15 Claims, 6 Drawing Sheets

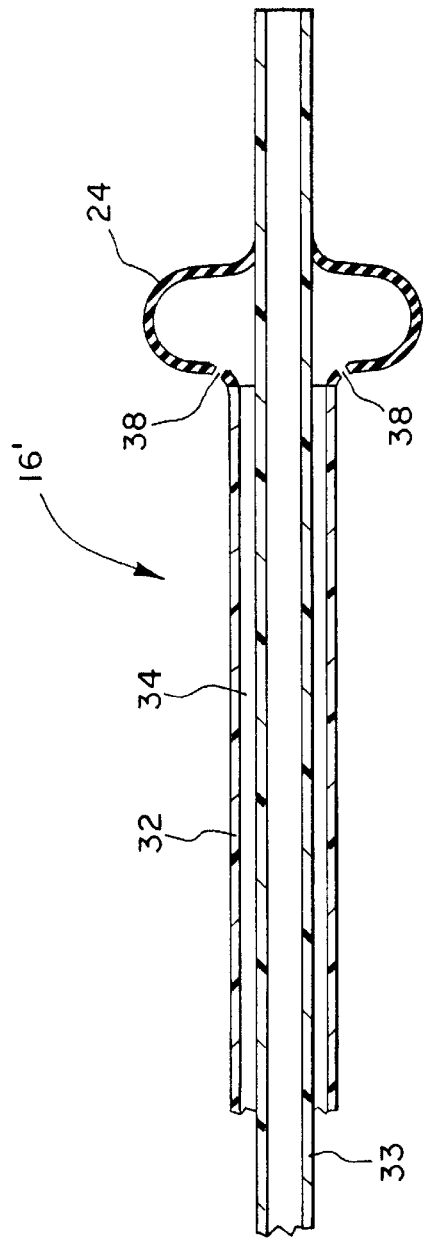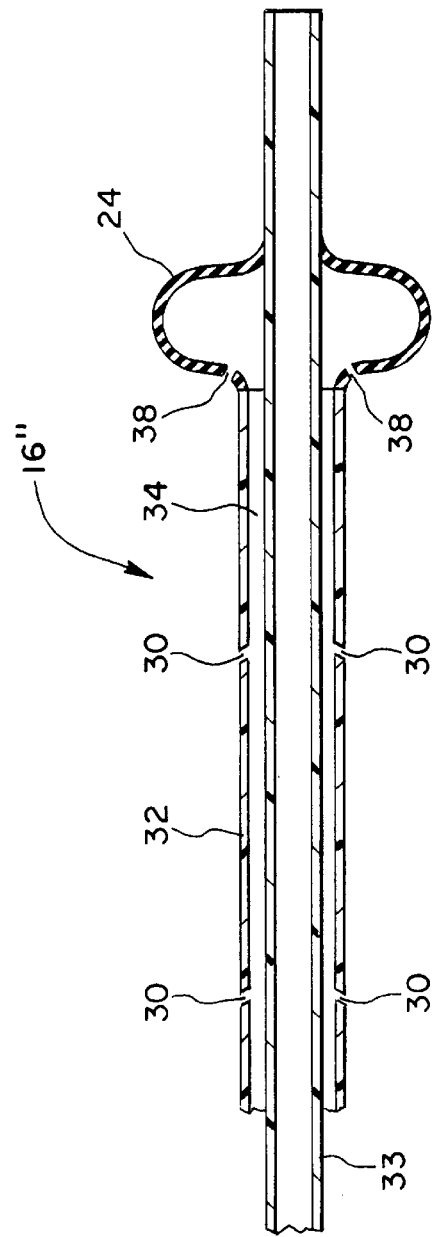

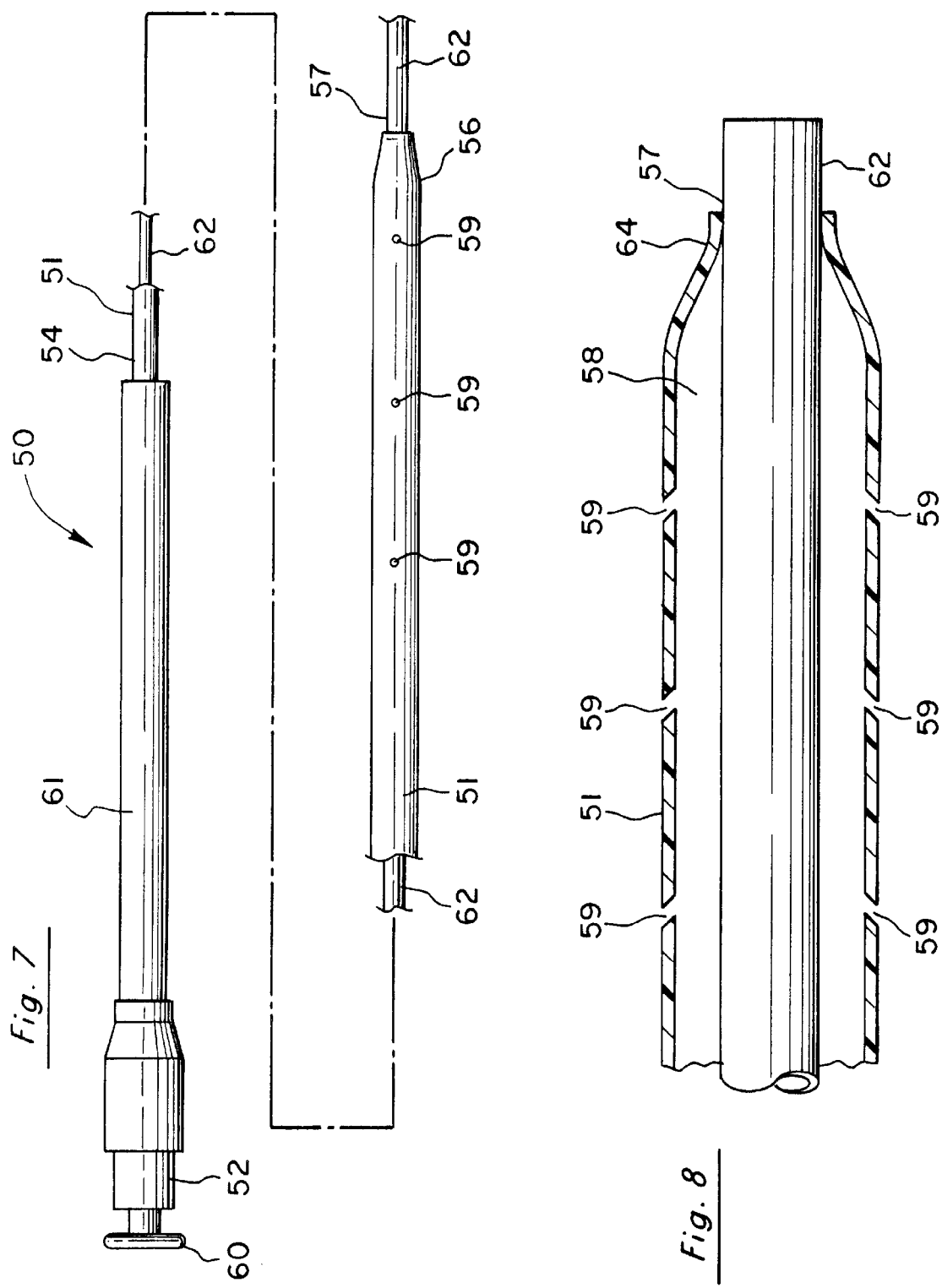

FLUID PROPULSION STEERABLE CATHETER AND METHOD

BACKGROUND OF THE INVENTION

The present invention relates generally to the structure and use of medical catheters. More particularly, the present invention relates to the construction and use of a fluid propulsion catheter designed to traverse a patient's vasculature to deliver fluids or other therapeutic agents into an anatomical lumen.

Delivery catheters are used for a variety of surgical applications, such as infusing therapeutic or diagnostic agents into a desired location within a patient's vasculature. To reach the target site, the catheter must be navigated through the patient's vasculature. This is often difficult due to the tortuous nature of the vasculature which can prevent forward motion of the catheter. One category of delivery catheters which have been proposed to address such problems and which are of particular interest to the invention are flow directed catheters. Flow directed catheters rely on the flow of blood through an artery to direct the catheter tip along the arterial flow path and to a target site.

Since flow directed catheters rely on blood flow to move the catheter body through the artery, the effectiveness of such catheters in traversing the artery can be limited by a variety of factors. For example, a patient's vasculature is often tortuous and access to distant vascular structures becomes difficult due to contact between the catheter body and the vascular walls. Flow directed catheters may also encounter partially occluded pathways, further hindering the catheter's ability to reach the target site. Additionally, flow directed catheters can be difficult to navigate into a specific vessel branch of a vascular tree since the distal end of the catheter will tend to follow the vessels possessing the highest rate of blood flow.

A variety of flow directed catheters have been proposed to address such problems. For example, one type of flow directed catheter uses an enlarged balloon or cup-shaped end to create a partial obstruction causing the blood flow to pull the tip of the catheter in the direction of the blood flow. See, for example, U.S. Pat. Nos. 3,995,623 to Blake et al. and 4,024,873 to Antoshkiw et al.

Another proposed catheter design is described in copending U.S. application Ser. No. 08/399,677, filed Mar. 7, 1995, now U.S. Pat. No. 5,601,538, the disclosure of which is herein incorporated by reference. Such a catheter includes a distal end which is constructed of a hydrophilic material. Such a design provides several advantages including improved flow properties because the hydrophilic material becomes, in effect, part of the bloodstream and is therefore carried along more effectively by the bloodstream.

Although many flow directed catheters have proven to be generally successful, it would be desirable to provide various improvements to assist a flow directed catheter in traversing the tortuous vasculature of a patient. In particular, it would be desirable to provide a flow directed catheter having the ability to propel itself through a body lumen, especially in regions where travel through the body lumen is particularly difficult due to partial occlusions or tortuous pathways. It would be further desirable if such a catheter were able to be steered into a desired branch of a vascular tree.

SUMMARY OF THE INVENTION

The present invention provides various flow directed catheter and method which rely at least in part on some form of fluid propulsion to move the catheter through a body lumen. In one exemplary embodiment, the invention provides a flow directed catheter comprising a catheter body having a proximal end, a distal end and at least one axial lumen. At least one jet is in fluid communication with the axial lumen. The jet is angled toward the proximal end of the catheter body so that a fluid which is flowed through the axial lumen exits the jet in a proximal direction to distally propel the catheter body. In this way, the catheter may be moved through a body lumen by the propulsive forces created by the jet. Moreover, if encountered, also the jet allows the catheter to be selectively steered into specific vessels of a vascular tree.

In one exemplary aspect, the jet comprises at least one channel extending from the axial lumen to an outer surface of the catheter body at an acute angle relative to the axial lumen. In another aspect, a balloon may alternatively be operably attached to the catheter body near the distal end. The balloon provides a partial obstruction in the vessel causing the blood flow to pull the catheter body in the direction of the blood flow. Preferably, the balloon is attached within about 10 cm of the distal end of the catheter body. Optionally, the balloon may be placed in fluid communication with the axial lumen so that the catheter may be provided with at least a second jet which is included on the balloon. Preferably such a jet will comprise at least one aperture which extends through a wall of the balloon in a proximal direction. With such a configuration, the catheter may be propelled by both the jet in the catheter body and the jet in the balloon. Alternatively, the catheter could be propelled by the jet in the balloon without the jet in the catheter body.

In still another aspect, the catheter body includes two axial lumens, with the jet being in fluid communication with one of the lumens. In one particular arrangement, the catheter body may comprise a first tubular body and a second tubular body which is disposed within and coaxially aligned with the first tubular body. In this manner, one of the axial lumens is formed between the two tubular bodies and the other axial lumen is formed within the second tubular body.

In another alternative aspect, a guide wire is provided and extends through the axial lumen. The catheter body includes a restriction distal to the jet to provide a fluidic seal between the catheter body and the guide wire. This fluidic seal allows fluid flowing through the axial lumen to exit the channel in the catheter body to create a proximally-facing jet.

The invention further provides an exemplary method for moving a catheter along a body lumen. The method comprises providing the catheter with a catheter body having a proximal end, a distal end and an axial lumen. At least one jet is in fluid communication with the axial lumen. With such a configuration, the distal end of the catheter body is introduced into the body lumen. A pressurized fluid is then introduced into the axial lumen so that the fluid exits the catheter through the jet in a generally proximal direction to distally propel the catheter within the body lumen.

In one exemplary aspect of the method, the jet comprises at least one channel extending from the axial lumen to an outer surface of the catheter body at an acute angle relative to the axial lumen. In this way, the fluid exiting the jet is proximally facing to distally propel the catheter body. In an alternative aspect, a balloon is operably attached to the catheter body near the distal end. With such a configuration, the blood flowing within the body lumen will come into contact with the balloon to assist in propelling the catheter within the body lumen. Optionally, the balloon may be placed in fluid communication with the axial lumen so that at least some of the pressurized fluid which is introduced into the axial lumen exits a second jet in a wall of the balloon in a generally proximal direction. In this way, the catheter may be propelled by both the jet in the balloon and the jet in the catheter body. It will be appreciated that the catheter could optionally be propelled by just the balloon jet.

In another aspect, the catheter body includes an opening at the distal end and a fluid delivery lumen which is separate from the axial lumen. With such a configuration, a therapeutic or diagnostic fluid may be introduced to a target region within the body lumen by introducing the fluid into the fluid delivery lumen where it will exit the opening at the distal end.

In still another aspect of the method, the catheter body includes a restriction distal to the jet. A guide wire is then introduced through the axial lumen to form a fluidic seal between the guide wire and the restriction. In this manner, the pressurized fluid may exit the catheter body through the jet to distally propel the catheter body.

Other features and advantages will appear from the following description in which the specific embodiments are set forth in detail in conjunction with the accompanying drawing.

BRIEF DESCRIPTION OF THE DRAWINGS

FIG. 3 is a detailed view of an alternative embodiment of the distal end of the catheter of FIG. 1 having a plurality of jets in a wall of the balloon.

FIG. 4 is a detailed view of still another alternative embodiment of the catheter of FIG. 1 having a plurality of jets in both the catheter body and the balloon.

FIG. 7 is a side view of yet another alternative fluid propulsion catheter according to the invention.

FIG. 8 is a detailed view of a distal end of the catheter of FIG. 7 showing a plurality of jets.

DESCRIPTION OF THE PREFERRED EMBODIMENT

The present invention provides various catheters and methods which rely at least in part on propulsive forces to distally-propel the catheter through a body lumen. The propulsive forces are also advantageous in allowing the catheter to be selectively steered into a specific vessel of a vessel tree. Preferably, such propulsive forces are created by providing the catheter with at least one fluid jet which produces a proximally directed, high pressure flow of fluid. Usually, such a jet will be constructed by forming a channel within the catheter body, by forming a channel within a wall of a balloon which in turn is attached to the catheter body, or both. In this manner, a fluid may be introduced through the catheter body where it will proximally exit through the channel in the catheter body and/or the balloon to distally propel the catheter. Although useful in most body lumens, the catheters of the present invention will find their greatest use in small lumens, such as the arteries within the heart and brain.

Figure 1:
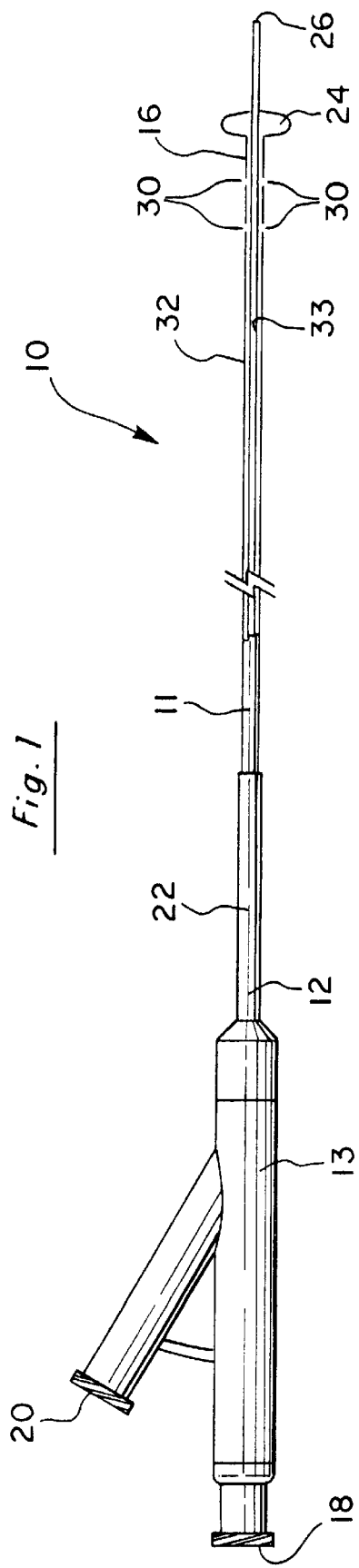
FIG. 1 is a side view of an exemplary fluid propulsion catheter having a balloon near a distal end according to the invention.

Referring now to FIG. 1, an exemplary embodiment of a flow directed, fluid propulsion catheter 10 will be described. Catheter 10 comprises a catheter body 11 having proximal end 12 and a distal end 16 having an open distal tip 26. The particular length of catheter body 11 will vary depending upon the particular application, and will usually have a length in the range from about 60 cm to about 175 cm, more preferably from about 150 cm to about 165 cm. Catheter body 11 has an outer diameter which is configured to be small enough to allow the catheter body to pass through the particular body lumen. For most vascular applications, catheter body 11 will preferably have an outer diameter which is in the range from about 0.5 mm to about 3 mm, and more preferably from about 1 mm to about 1.5 mm.

Distal end 16 is preferably constructed to be soft and flexible so that it will be able to more easily traverse tortuous vessels. Catheter is preferably provided with a lubricous surface which may be fabricated by modifying the surface of the catheter body or by applying a secondary coating. For example, a hydrophilic coating may be placed onto the catheter body. Optionally, distal end 16 may be constructed of a hydrophilic material as described in copending U.S. application Ser. No. 08/399,677, now U.S. Pat. No. 5,601,538, previously incorporated by reference.

Proximal end 12 conveniently includes strain relief 22 to protect the catheter during insertion. Proximal end 12 is connected to a hub 13 which includes a balloon inflation/propulsion port 20 and a therapeutic fluid port 18. Attached to catheter body 11 at distal end 16 is an inflatable balloon 24. Balloon 24 is inflated by introducing a fluid through balloon inflation/propulsion port 20. Fluids introduced through port 20 also serve to produce a propulsive jet as described in greater detail hereinafter. Therapeutic fluid port 18 allows fluids or other diagnostic or therapeutic agents to reach a target area within the patient after exiting through distal tip 26.

When inflated, balloon 24 functions as a sail to engage the blood stream and thus assist in moving catheter 10 through a body lumen. When inflated, balloon 24 is preferably about 0.5 mm to about 10 mm in diameter and more preferably from about 2 mm to 3 mm in diameter. Balloon 24 is preferably located within about 10 cm of distal tip 26, and more preferably within about 5 cm of distal tip 26. Balloon 24 may be affixed to the distal end 16 using a variety of methods, such as by constructing balloon 24 from a polymeric material and then heat bonding the balloon to the distal end of catheter body 11.

Figure 2:
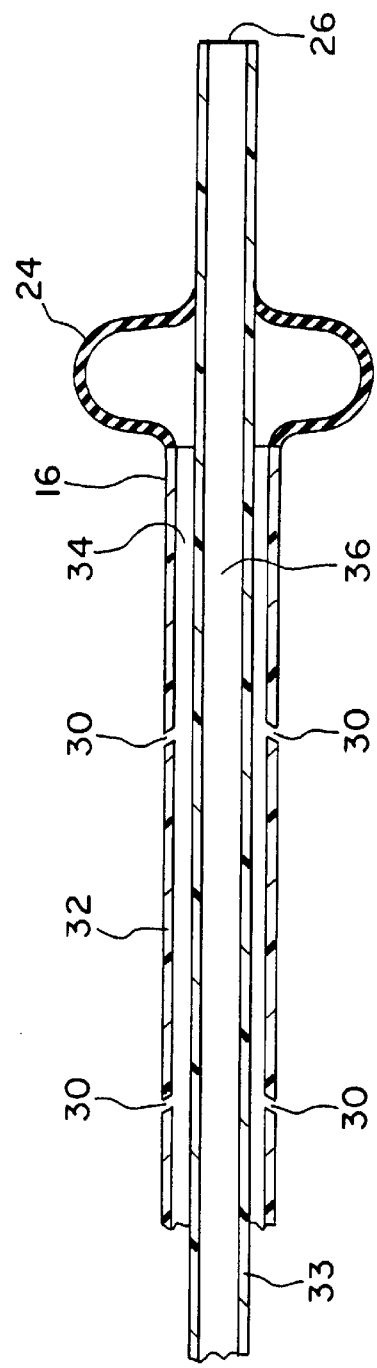
FIG. 2 is a detailed view of the distal end of the catheter of FIG. 1 having a plurality of jets.

As best shown in FIG. 2, catheter body 11 comprises an outer tubular body 32 and an inner tubular body 33. Formed within outer body 32 at distal end 16 are a plurality of channels 30 which function as fluid jets to propel catheter 10 through a body lumen when a pressurized fluid exits the catheter body 11 through the channels. Channels 30 may be formed in a number of ways, such as, for example, by inserting a heated, sharpened mandrel into outer body 32. Channels 30 are preferably formed at an acute angle relative to a central axis of the catheter body, preferably at an angle in the range from about 1 degrees to about 89 degrees relative to proximal end 12 so that the exiting fluid jets will be proximally divided.

The fluids employed to create the fluid jets are introduced into port 20 where they pass through an axial lumen 34 formed between outer body 32 and inner body 33. Since the fluids will be pressurized, it is desirable to construct tubular bodies 32 and 33 of materials which will maintain their integrity under high pressures (while remaining relatively thin). Exemplary materials for constructing tubular bodies 32 and 33 include LDPE, PEBA, pollyurethanes, polyethelene, and the like. Inner body 33 may optionally include a braided reinforcement to prevent it from collapsing.

The size and arrangement of channels 30 is selected so that the exiting fluid will create jets which are sufficient to distally propel the catheter. Preferably, channels 30 will have a diameter in the range from about 0.1 mm to about 0.5 mm. The number of channels in catheter body 11 will vary depending upon the particular application. In one preferable configuration, catheter body 11 includes three pairs of jets (with the channels of each pair being on opposite sides of outer body 32) which are located about 10 cm, 30 cm, and 50 cm proximal of distal tip 26.

Still referring to FIG. 2, inner body 33 defines an inner lumen 36 which provides a fluid path for the delivery of fluids or other diagnostic or therapeutic agents to a target area within the patient. Such fluids may be introduced into port 18 where they will pass through lumen 36 and exit distal tip 26.

Although shown with two coaxial lumens, it will be appreciated that other arrangement of catheter body 11 are possible. For example, catheter body 11 may be constructed of a single tubular body defining a central lumen, with a second lumen being formed within a wall of the tubular body.

With the arrangement shown in FIGS. 1 and 2, catheter 10 is able to traverse a patient's vasculature by having its distal end propelled with various jets. In this way, catheter 10 need not rely solely on the flow of body fluids to move the catheter body through the vasculature. Moreover, the jets allow the catheter body to be selectively steered through the vasculature. This feature is important when introducing the catheter into a particular branch of a vascular tree. The jets allow the distal end to be steered into a desired branch, even if the blood flow rate through the desired branch is significantly less than through other branches.

Referring now to FIG. 3, an alternative arrangement of a distal end 16' of catheter 10 will be described. Distal end 16' of FIG. 3 is essentially identical to distal end 16 of FIG. 2 except that distal end 16' does not include channels 30 in outer body 32. For convenience of discussion, similar elements will be referred to using the same reference numerals used in FIGS. 1 and 2. Instead if relying upon channels in the catheter body, distal end 16' employs a plurality of apertures 38 which are formed within the walls of balloon 24 to form the propulsive jets. Apertures 38 are configured to be proximally facing so that as fluids exit apertures 38, a proximally directed fluid jet is produced to distally propel catheter 10. Fluids used to produce the jets from apertures 38 are introduced into port 20 where they pass through lumen 34 as previously described.

FIG. 4 illustrates another alternative arrangement of a distal end 16" of catheter 10. Distal end 16" is essentially identical to distal end 16 of FIG. 2 except that distal end 16" also includes apertures 38 in balloon 24 similar to those shown in the embodiment of FIG. 3. In this way, distal end 16" includes both the channels 30 of the embodiment of FIG. 2 and apertures 38 of the embodiment of FIG. 3. With this arrangement, jets are formed both in catheter body 11 and in balloon 24 as a fluid is passed through lumen 34 to distally propel and steer catheter 10 through the vasculature.

Figure 5:
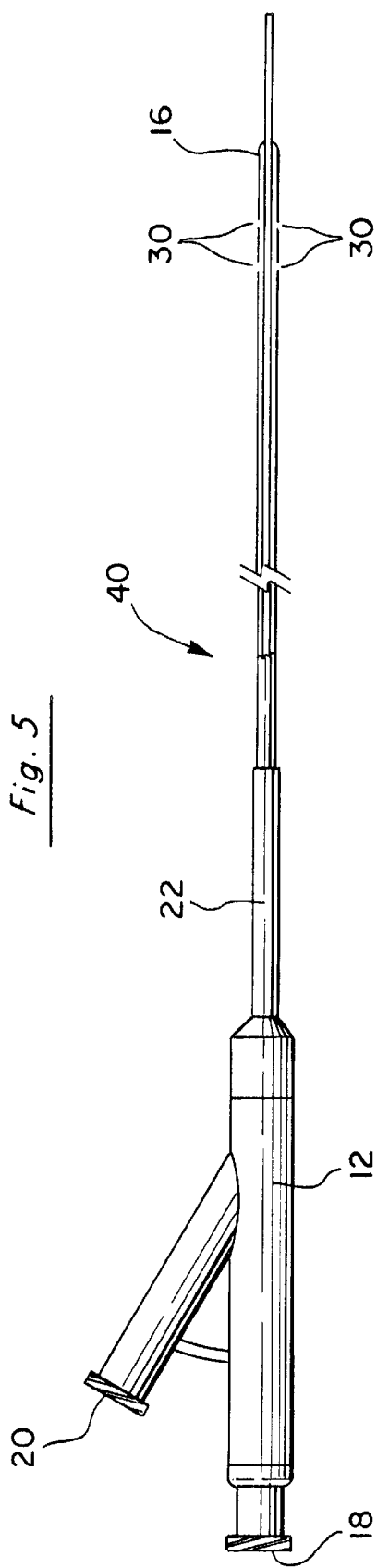
FIG. 5 is a side view of an alternative fluid propulsion catheter according to the invention.
Figure 6:
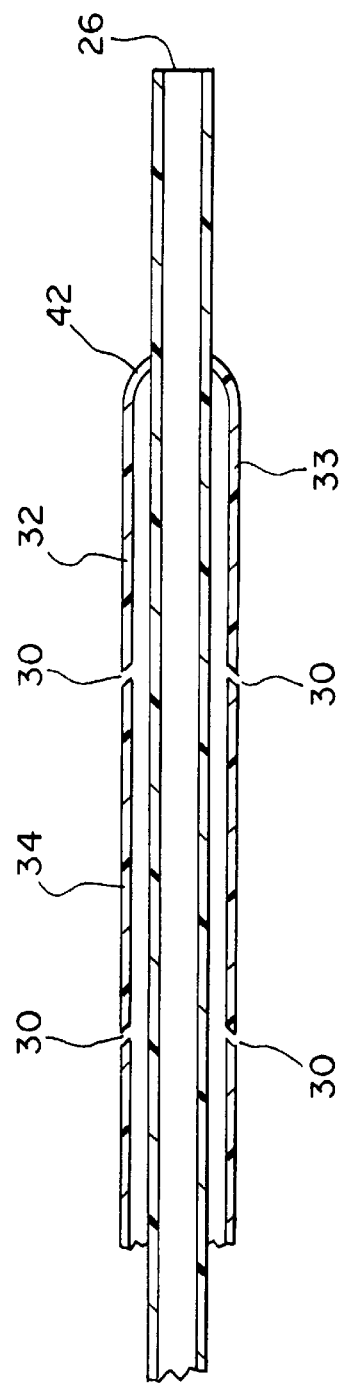
FIG. 6 is a detailed view of a distal end of the catheter of FIG. 5 having a plurality of jets.

Referring to FIGS. 5 and 6, a further alternative embodiment of a flow directed, fluid propulsion catheter 40 will be described. Catheter 40 is essentially identical to catheter 10 of FIG. 1 except that it does not have a balloon. For convenience of discussion, the same reference numerals used to describe catheter 10 will be used in connection with catheter 40.

Catheter 40 includes a plurality of channels 30 which are employed to produce fluid jets when a fluid is introduced into port 20 as previously described in connection with catheter 10. To prevent the fluid in lumen 34 from exiting at distal end 16, a seal 42 is provided between outer body 32 and inner body 33 as shown. All other features are essentially identical to catheter 10. By removing the balloon from catheter 40, the catheter is better able to traverse small and tortuous arteries that would otherwise difficult or impossible with a balloon design.

Referring to FIG. 7, still a further alternative embodiment of a flow directed, fluid propulsion catheter 50 will be described. Catheter 50 comprises a catheter body 51 having a proximal end 52, a midsection 54, and a distal end 56 having an open distal tip 57. Catheter body 51 may be constructed similar to the catheter described in copending U.S. application Ser. No. 08/572,821, pending, filed Dec. 14, 1995, the disclosure of which is herein incorporated by reference. As illustrated in FIG. 8, a central lumen 58 extends the length of catheter body 51. Formed within the walls of catheter body 51 are a plurality of channels 59 which are in fluid communication with central lumen 58. Channels 59 are at an acute angle relative to central lumen 58 and serve to produce a propulsine fluid jet when a fluid exits lumen 58 through channels 59. Channels 59 may be constructed similar to channels 30 as previously described. Conveniently, catheter 50 further includes a stiff outer sheath 61 at proximal end 52 which allows catheter body 51 to be pushed through the patient's vasculature upon initial introduction into the patient.

Central lumen 58 is also in fluid communication with a fluid introduction port 60 at proximal end 52 and with distal tip 57. Extending through port 60, central lumen 58 and distal tip 57 is a guide wire 62. As shown in FIG. 8, catheter body 51 includes a restriction 64 at distal end 56 which forms a fluidic seal when guide wire 62 is placed therein. In this way, fluids introduced through port 60 will exit catheter body through channels 59 to produce to propulsive jets. The jets propel the catheter body along guide wire 62 until distal end 56 is at the desired location. A therapeutic or diagnostic agent may then be introduced to the target site by withdrawing guide wire 62 from distal tip 57 and introducing the fluid through port 60.

Figure 9:
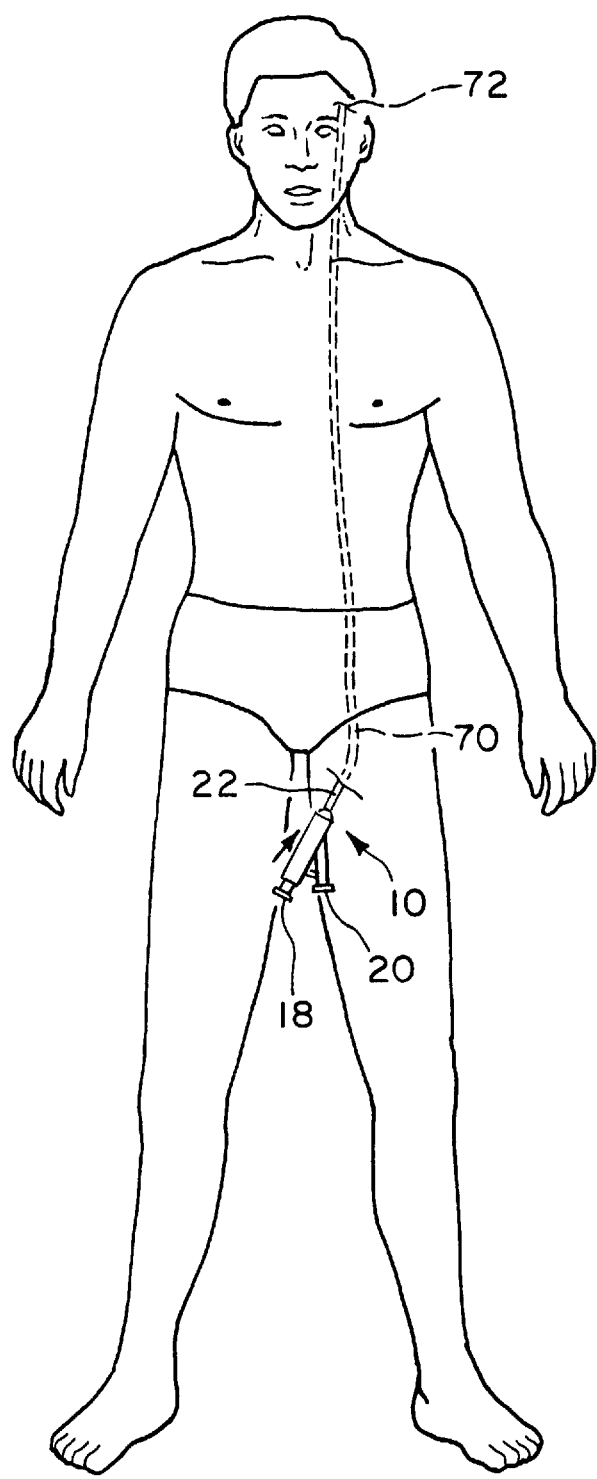
FIGS. 9 and 10 illustrate an exemplary method for moving a catheter through a body lumen according to the invention.
Figure 10:
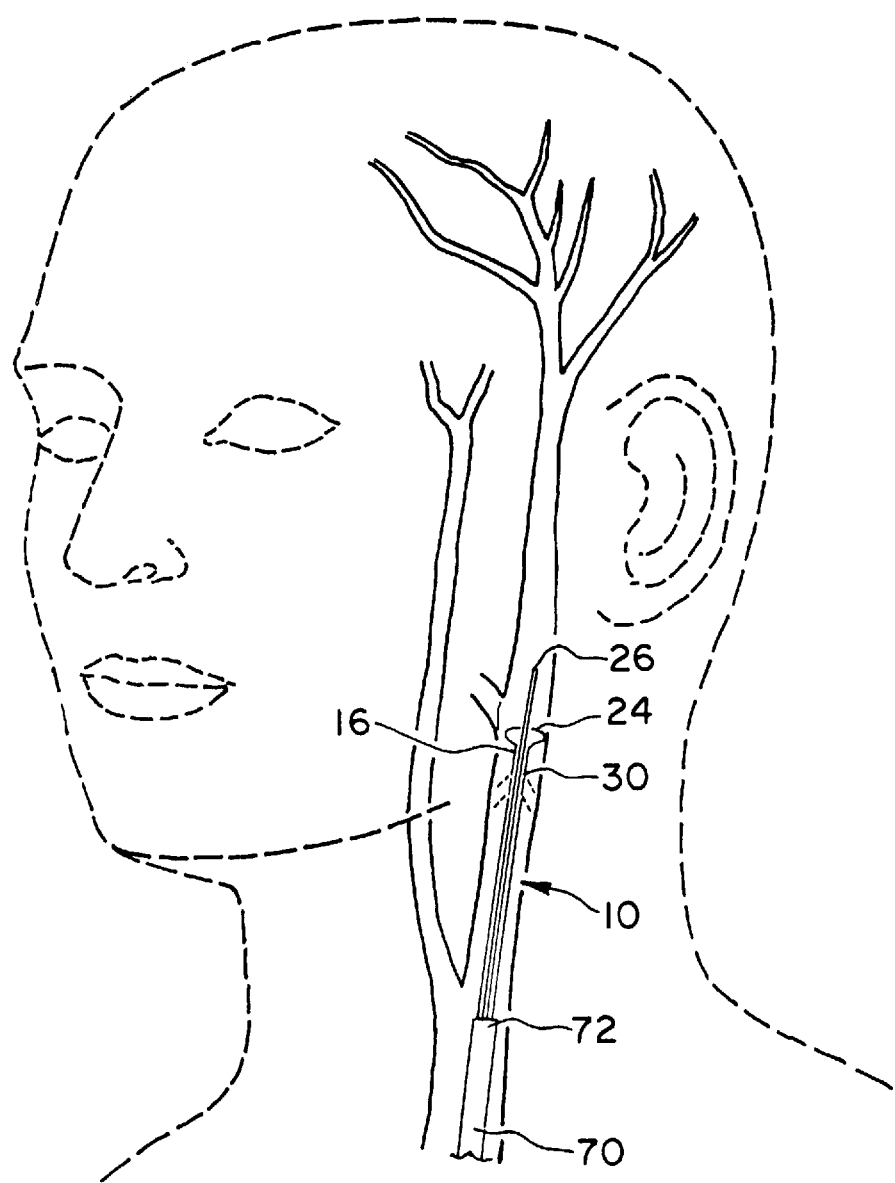

Referring to FIGS. 9 and 10, an exemplary method for delivering a fluid to a target site within a body lumen will be described. For convenience of discussion, the method will refer to the catheter of FIGS. 1 and 2, although the method is also applicable to the other alternative embodiments described herein. Initially, a guide catheter 70 is placed into the femoral artery of the patient, through descending aorta, aortic arch and common cardioid arteries so that a tip 72 of guide catheter 70 is located in a distal artery, often in the patient's head.

Catheter 10 is then introduced into the patient through guide catheter 70 until distal tip 26 reaches tip 72 of guide catheter 70, with the stiffness of sheath 22 allowing for catheter 10 to be pushed through guiding catheter 70. At this point, distal end 16 is pushed beyond tip 72 of guide catheter 70 where the flow of fluids through the body lumen will tend to pull the catheter further into the body lumen. As shown in FIG. 10, fluid jets are produced through channels 30 by introducing a pressurized fluid into port 20 (see FIG. 1). The jets further assist in moving catheter 10 through the body lumen by providing a propulsive force. If needed, the jets may also serve to steer distal end 16 into a desired branch of a vascular tree.

When distal end 16 is at the desired location, the jets are stopped and a therapeutic or diagnostic agent is introduced into port 18 (see FIG. 1) where it exits distal tip 26 at the desired location.

Although the foregoing invention has been described in detail for purposes of clarity of understanding, it will be appreciated that certain modifications may be practice within the scope of the appended claims.

What is claimed is:

1. A flow directed catheter comprising:
    a catheter body comprising a tubular member having a proximal end, a distal end and at least one axial lumen;
    a balloon operably attached to the catheter body near the distal end;
    at least one jet formed in the wall of said tubular member in fluid communication with the axial lumen, the jet being located between the balloon and the proximal end of the tubular member and being angled toward the proximal end of the catheter body so that a fluid which is flowed through the axial lumen exits the jet to distally propel the catheter body.

2. A catheter as in claim 1, wherein the jet comprises at least one channel extending from the axial lumen to an outer surface of the catheter body at an acute angle relative to the axial lumen.

3. A catheter as in claim 2, wherein the balloon is in fluid communication with the axial lumen, and further comprising at least a second jet, said second jet comprising at least one aperture extending through a wall of the balloon.

4. A catheter as in claim 2, further comprising a guide wire extending through the axial lumen, and wherein the catheter body includes a restriction distal to the jet to provide a fluidic seal between the catheter body and the guide wire.

5. A catheter as in claim 1, wherein the balloon is in fluid communication with the axial lumen, and further comprising a second jet which comprises at least one aperture extending through a wall of the balloon.

6. A catheter in claim 1, further comprising a plurality of jets.

7. A catheter as in claim 1, wherein the catheter body includes two axial lumens, with the jet being in fluid communication with one of the lumens.

8. A catheter as in claim 7, wherein the catheter body comprises a first tubular body and a second tubular body disposed within and coaxially aligned with the first tubular body, with one of the axial lumens being formed between the two tubular bodies and the other axial lumen being formed within the second tubular body.

9. A catheter as in claim 1, wherein the balloon is within about 10 cm of the distal end of the catheter body.

10. A method for moving a catheter along a body lumen, the method comprising:
    providing the catheter with a catheter body having a proximal end, a distal end and an axial lumen and at least one jet in fluid communication with the axial lumen;
    introducing the distal end of the catheter body into the body lumen; and
    introducing a pressurized fluid into the axial lumen so that the fluid exits the catheter through the jet in a generally proximal direction to distally propel the catheter within the body lumen;
    wherein the catheter further includes a balloon which is operably attached to the catheter body near the distal end and which is in fluid communication with the axial lumen, and wherein the jet comprises at least one aperture extending through a wall of the balloon.

11. A method as in claim 10, wherein the pressurized fluid exits the catheter through a plurality of jets in a generally proximal direction.

12. A flow directed catheter comprising:
    a catheter body having a proximal end, a distal end and at least one axial lumen;
    at least one jet in fluid communication with the axial lumen, the jet being angled toward the proximal end of the catheter body, whereby a fluid which is flowed through the axial lumen exits the jet to distally propel the catheter body, wherein the jet comprises at least one channel extending from the axial lumen to an outer surface of the catheter body at an acute angle relative to the axial lumen;
    a balloon operably attached to the catheter body near the distal end, wherein the balloon is in fluid communication with the axial lumen; and
    at least a second jet, said second jet comprising at least one aperture extending through a wall of the balloon.

13. A method for moving a catheter along a body lumen, the method comprising:
    providing the catheter with a catheter body having a proximal end, a distal end and an axial lumen and at least one jet in fluid communication with the axial lumen, wherein the jet comprises at least one channel extending from the axial lumen to an outer surface of the catheter body at an acute angle relative to the axial lumen;
    introducing the distal end of the catheter body into the body lumen; and
    introducing a pressurized fluid into the axial lumen so that the fluid exits the catheter through the jet in a generally proximal direction to distally propel the catheter within the body lumen;
    wherein the catheter further includes a balloon operably attached to the catheter body near the distal end, wherein blood flow within the body lumen comes into contact with the balloon to assist in moving the catheter through the body lumen, wherein the balloon is in fluid communication with the axial lumen, and wherein at least some of the pressurized fluid introduced into the axial lumen exits a second jet in a wall of the balloon in a generally proximal direction.

14. A method for moving a catheter along a body lumen, the method comprising:
    providing the catheter with a catheter body having a proximal end, a distal end and an axial lumen and at least one jet in fluid communication with the axial lumen;
    introducing the distal end of the catheter body into the body lumen; and
    introducing a pressurized fluid into the axial lumen so that the fluid exits the catheter through the jet in a generally proximal direction to distally propel the catheter within the body lumen;

wherein the catheter body includes a restriction distal to the jet, and further comprising introducing a guide wire through the axial lumen to form a fluidic seal between the guide wire and the restriction, whereby the pressurized fluid may exit the catheter body through the jet.

15. A method for moving a catheter along a body lumen, the method comprising:

providing the catheter with a catheter body having a proximal end, a distal end and an axial lumen and at least one jet in fluid communication with the axial lumen;

wherein the catheter further includes a balloon operably attached to the catheter body near the distal end;

introducing the distal end of the catheter body into the body lumen; and introducing a pressurized fluid into the axial lumen so that the fluid exits the catheter through the jet in a generally proximal direction to distally propel the catheter within the body lumen;

wherein the catheter body includes an opening at the distal end and a fluid delivery lumen separate from the axial lumen, and further comprising introducing a therapeutic or diagnostic fluid into the fluid delivery lumen and out the opening at the distal end when the catheter body is at a target region within the body lumen.

* * * * *